United States Patent [19]

Behme

[11] Patent Number: 4,967,629

[45] Date of Patent: Nov. 6, 1990

[54] MICROTOME

[75] Inventor: Werner Behme, Wiesloch, Fed. Rep. of Germany

[73] Assignee: Microm Laborgerate GmbH, Heidelberg, Fed. Rep. of Germany

[21] Appl. No.: 306,587

[22] Filed: Feb. 6, 1989

[30] Foreign Application Priority Data

Feb. 27, 1988 [DE] Fed. Rep. of Germany ....... 3809269

[51] Int. Cl.$^5$ .............................................. G01N 1/06
[52] U.S. Cl. ........................................ 83/714; 83/414; 83/718; 83/915.5
[58] Field of Search ................ 83/412, 414, 713, 714, 83/715, 717, 718, 915.5

[56] References Cited

U.S. PATENT DOCUMENTS

| | | | |
|---|---|---|---|
| 3,293,972 | 12/1966 | Burkhardt et al. | 83/915.5 |
| 3,628,411 | 12/1971 | Shatzel | 83/915.5 |
| 3,771,405 | 11/1973 | Blum | 83/915.5 |
| 4,150,593 | 4/1979 | Butler | 83/915.5 |
| 4,484,503 | 11/1984 | Sitte et al. | 83/915.5 |
| 4,594,929 | 6/1986 | Behme et al. | 83/915.5 |
| 4,625,608 | 12/1986 | Behme et al. | 83/915.5 |

Primary Examiner—Frank T. Yost
Assistant Examiner—Scott A. Smith
Attorney, Agent, or Firm—Elliot M. Olstein; Raymond J. Lillie

[57] ABSTRACT

A microtome has a frame structure in which an object holding member for holding an object to be thinly cut is movable with an oscillating movement by a drive device. The object holding member has a cutting thickness feed member and an object return member, the latter including a switch element disposed on the object holding member for oscillating movement therewith. The frame structure carries first and second abutments arranged at the respective end portions of the path of movement of the switch element which oscillates with the object holding member. The switch element is thus displaceable by co-operation with the first and second abutments between first and second positions respectively; when the switch element is in its first position the object holding member is in a position in which it is set back from the cutting plane while when the switch element is in its second position the object holding member is in a position of being advanced into the cutting plane for an object-cutting operation.

6 Claims, 1 Drawing Sheet

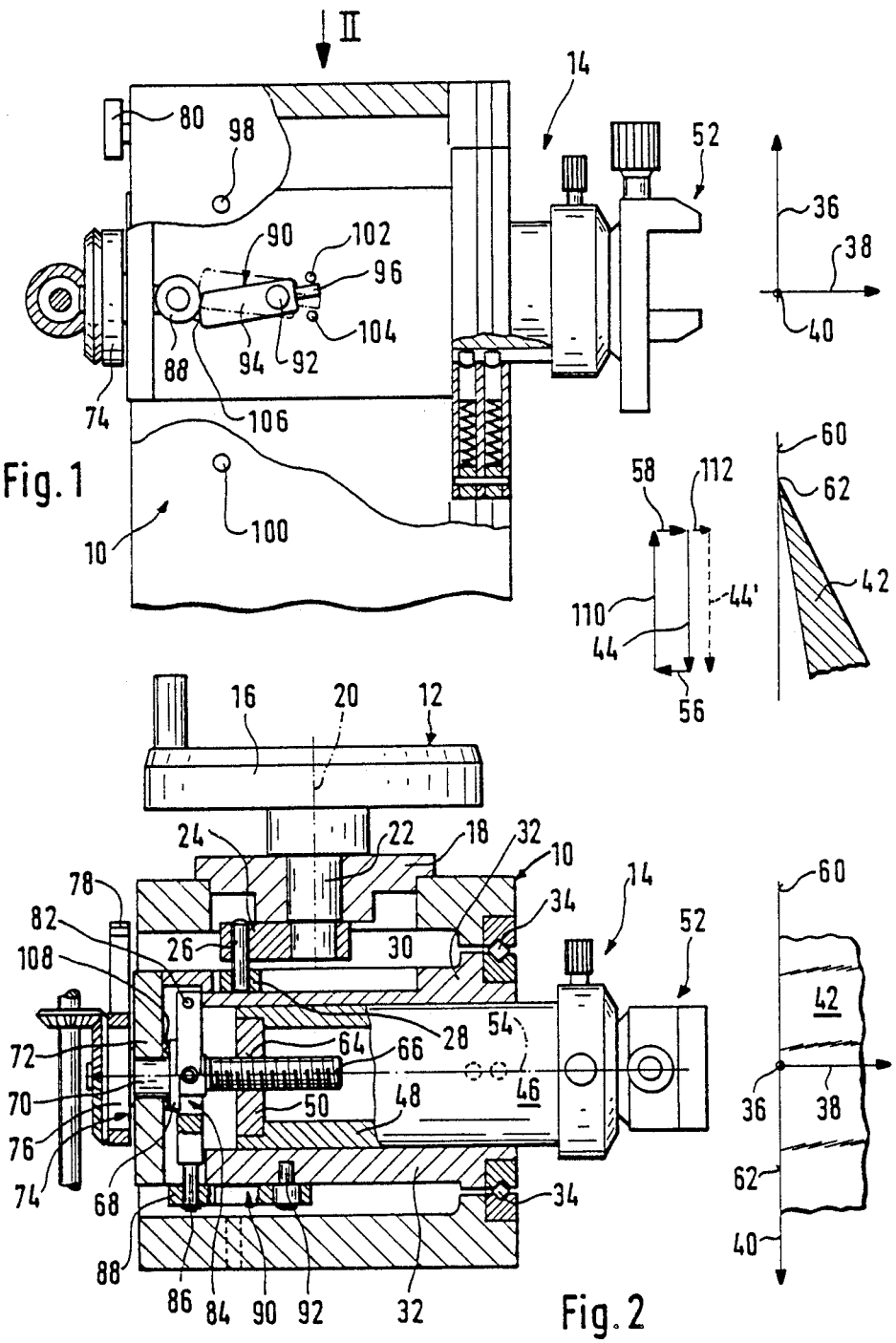

MICROTOME

BACKGROUND OF THE INVENTION

The invention relates generally to a microtome.

One form of microtome, as is disclosed for example in DE 34 04 098 Cl, comprises an object holding means which is movable with a linear oscillating movement in a frame structure by means of a drive device, and further comprises a cutting thickness feed means which is provided on the object holding means for advancing the object holding means during a drive cycle by a defined distance in its axial direction relative to the cutting plane which is defined by a cutting blade or knife. That microtome further includes an object return means co-operable with the object holding means for returning the object holding means by a given distance from the cutting plane defined by the blade or knife, after the cutting operation has been carried out. In that microtome structure, the object return means has a frame-like member with a sensing device, the sensing device bearing against a cam disc. The cam disc is operatively connected to the drive means which may be for example a drive hand wheel. Provided between the frame-like member of the object return means and the frame structure of the microtome are spring members for urging the frame-like member towards a lever with which the object holding means can be actuated, to perform a return movement. The eccentric disc and the frame-like member of the object return means not only take up a certain amount of space but they are also relatively expensive to produce.

SUMMARY OF THE INVENTION

An object of the present invention is to provide a microtome which is of a comparatively simple design configuration.

A further object of the invention is to provide a microtome having an object return means for returning the object after a cutting operation, which is of a simple and compact construction while being reliable in operation.

Still another object of the present invention is to provide a microtome which is positive and precise in operation without involving major mechanical complexity and maintenance operations.

In accordance with the principles of the present invention, these and other objects are achieved by a microtome comprising an object holding means movable with a linear oscillating movement in a frame structure by operation of a drive means. The microtome has a cutting thickness feed means on the object holding means for advancing the latter during a drive cycle by a defined distance in its axial direction relative to a cutting plane defined by a cutting blade or knife. An object return means co-operates with the object holding means to return same by a given distance from the cutting plane after a cutting operation has been carried out. The object return means includes a switch element arranged on the object holding means, while the frame structure is provided with first and second abutments. The abutments are arranged on the end portions of the path of movement of the switching element which oscillates with a linear motion with the object holding means. The switch element is displaceable by the two abutments between first and second positions, wherein in the first position of the switch element the object holding means is disposed in a position in which it is set back from the cutting plane and in the second position of the switch element the object holding means occupies the position of being advanced into the cutting plane.

The microtome including the object return means as set forth above may be a rotational microtome as well as a carriage-type microtome. It is particularly advantageous for the microtome incorporating the object return means as defined above to be a rotational microtome.

In a construction in accordance with the invention in which the object holding means has a guide member which is movable with a linear oscillating movement by the drive means in a first direction in space and in which a cylindrical member of the object holding means, provided with an object clamping means, is movable stepwise in a second direction which is normal to said first direction, the object clamping means, during a drive cycle, performing a movement referred to as a pilgrim stepping movement consisting of a cutting movement in the first direction, a subsequent return movement in the second direction, thereby increasing the mechanical stressing of a spring element, a reversal movement following the return movement, in said first direction, with the spring element in a stressed condition, and a subsequent advance movement caused by a reduction in said increased spring stressing, as well as a feed movement produced by the cutting thickness feed means, wherein the reversal movement and the cutting movement or the return movement and the advance movement respectively are each of the same amplitude and are in opposite relationship to each other, it has been found advantageous for the switch element to be in the form of a lever and to be arranged on the guide member of the object holding means in such a way that in one position of the switch element the mechanical stressing of the spring element is increased and in the second position of the switch element the increased spring stressing is reduced.

In the case of a rotational microtome, that arrangement provides a switch element which is of a simple design and which permits a precise stepping movement as outlined above to be carried out, in conjunction with the cutting thickness feed means, during a drive cycle of the machine. The switch element which is in the form of a lever is disposed on the guide member of the object holding means so that it performs the oscillating movement in the first direction in space, corresponding to the guide member, when the microtome is driven by its drive means. The drive means may be any suitable form of drive means such as a drive motor or a drive hand wheel.

The spring element is disposed between the object holding means and the cutting thickness feed means in such a way that at any time it has a certain level of mechanical prestressing which is increased during the return movement and held at a constant level during the reversal movement following the return movement. The mechanical prestressing of the spring element, at all times, means that the microtome is precise in operation while, as a single spring element may be sufficient, the microtome can also be of a simple, inexpensive construction which is easy to assemble and use.

In a preferred embodiment of a microtome in accordance with the principles of the invention, the cutting thickness feed means has a screwthreaded spindle which is arranged in said second direction in space and the object holding means is mounted for linear displacement, while being prevented from rotation, in the guide member, and is formed with a portion having a female screwthread therein, through which the screwthreaded spindle is screwed. The spring element is clamped between the guide member and the screwthreaded spindle and a lever element is mounted with its one end portion on the guide member, being pivotable about an axis which is arranged in said first direction in space. The lever element extends in a plane substantially normal to the second direction and bears against the screwthreaded spindle. The second end portion of the lever element co-operates with the object return means. The switch element of the object return means is pivotable on the guide member about an axis which is oriented in a third direction in space normal to the first and second directions. The switch element acts with its second end portion on the second end portion of the lever element, to increase the spring stressing of the spring element. While the switch element acts on the lever element, the latter is pivoted about its axis which is oriented in said first direction, while the spring element disposed between the lever element and the guide member of the object holding means is mechanically stressed. At the same time, in that condition, the screwthreaded spindle is set back by a given distance from the cutting plane so that, during the return movement of the object holding means, the specimen which is gripped in the object holding means and which is to be thinly cut does not drag or rub along the cutting blade.

In a preferred feature of the invention the end portion of the switch element, which acts on the lever element, has a curved switching surface, thereby providing a switching performance which is gentle and not abrupt, that is to say, giving a gentle smooth return movement, thus avoiding undesirable vibration of the microtome. In addition, the loading on the spring element is kept to a minimum by virtue of the switch element being designed with a curved switching surface.

In accordance with another preferred feature of the invention the switch element may be in the form of a double-armed lever, the first lever arm which acts on the lever element being longer than the oppositely disposed second lever arm of the switch element. It will be appreciated that it would be possible for the switch element to be in the form of a single-armed lever. In that respect, a point of particular importance is that the first lever arm which acts on the lever element can readily co-operate with the abutments which are disposed at stationary locations on the frame structure and which are arranged at the end portions of the path of movement of the switch element which oscillates in a linear motion with the object holding means, thereby to provide for switching over of the switch position of the lever-like switch element when the object holding means, after having performed a cutting movement, is in the one limit position or, after having carried out an object return and reversal movement, is in the opposite second limit position. The switch element may also co-operate with the lever element in such a way that actuation of the switch element does not occur only in the two limit positions, but already takes place shortly after a cutting movement has been performed and before the object holding means reaches the respective limit position thereof. That configuration provides a stepping movement as outlined above, which is not an angular or jerky movement, but a rounded smooth movement configuration.

In another preferred feature of the invention the second lever arm of the switch element, when in the form of a double-armed lever, may extend between third and fourth abutments on the guide member. The third and fourth abutments are provided for defining the switching movement of the switch element, which is triggered off or produced by the first and second abutments. Such a microtome structure further enhances the level of switching accuracy and operational reliability of the arrangement.

Further objects, features and advantages of a microtome in accordance with the principles of the present invention will be apparent from the following description of a preferred embodiment thereof.

BRIEF DESCRIPTION OF THE DRAWING

FIG. 1 is a partly cut-away side view of essential components of the microtome according to the invention, and FIG. 2 is a partly sectional view of the microtome shown in FIG. 1, viewing in the direction indicated by the arrow II therein.

DESCRIPTION OF THE PREFERRED EMBODIMENT

Reference is now made to the drawings showing a microtome, in particular a rotational microtome, comprising a frame structure which is generally indicated at 10, and provided with a drive means 12 for driving an object holding means 14. The drive means 12 comprises a hand wheel which is indicated at 16 in FIG. 2 and which is mounted rotatably about a longitudinal centre line 20 in the frame structure 10 by means of a bearing arrangement 18. An eccentric lever indicated at 24 in FIG. 2 is non-rotatably connected to the hand wheel 16 by way of a shaft 22 mounted in the bearing arrangement 18. Projecting from the eccentric lever 24 on the side remote from the hand wheel 16 is a pin 26 on which there is disposed a roller 28 or a slide member. The pin 26 with the roller 28 or the slide member projects into a slot 30 in a guide member 32 of the object holding means 14. The slot 30 in the guide member 32 is preferably oriented in a horizontal direction. The guide member 32 is mounted for linear movement in the frame structure 10 of the microtome by means of linear guide or mounting arrangements indicated at 34 in FIG. 2. The linear guide arrangements 34 extend in a first direction in space which is indicated by an arrow 36 in FIG. 1 and which is normal to the plane of the drawing in FIG. 2. Arrow 38 in FIGS. 1 and 2 indicates a second direction in space which is normal to the first direction 36. In FIG. 2, an arrow 40 indicates a third direction in space which is normal to the first and second directions 36 and 38 and which is normal to the plane of the drawing in FIG. 1.

Turning the hand wheel 16 of the drive means 12 about the longitudinal centre line 20 produces a corresponding rotary movement of the eccentric lever 24 and, by means of the roller 28 or slide member which engages into the slot 30, that produces a linearly oscillating movement of the object holding means 14 in the first direction 36.

Reference numeral 42 in the drawings indicates part of a cutting blade or knife for cutting off a thin section from an object (not shown) which is held in the object holding means 14, during a cutting movement. The cutting movement is indicated by an arrow 44 in FIG. 1.

Reference numeral 46 in FIG. 2 indicates a cylindrical member which is mounted in the guide member 32 and which is movable in the second direction 38. The member 46 has a cylindrical sleeve portion 48 which is closed off at one end by a cover element 50. At the second end portion of the member 46, which is in opposite relationship to the cover element 50, is a per se known object clamping means indicated generally at 52 which is provided for clamping an object which is to be thinly cut. The member 46 is disposed in the guide member 32 of the object holding means 14 in such a way as to be displaceable in the direction of the longitudinal axis 54 which is oriented in the second direction 38, while however being prevented from rotating. The member 46 can only be moved with an oscillating movement in the second direction 38 along the longitudinal axis 54. That oscillating movement is indicated by the arrows 56 and 58 in FIG. 1. The arrow 56 represents what is referred to as a return movement while the arrow 58 represents an advance movement 58 which is of an amplitude corresponding to the return movement 56. By virtue of the return movement as indicated by the arrow 56, the object holding means 14 and therewith an object which is clamped in the object clamping means 52 and which is to be thinly cut is moved away from the cutting plane 60, while the advance movement as indicated by the arrow 58 causes the object to be moved forward again to the cutting plane as indicated at 60 in FIG. 1, by a distance corresponding to the distance covered in the above-mentioned return movement. The cutting plane 60 is disposed in the first and third directions in space 36 and 40 and is defined by the cutting edge 62 of the cutting blade 42.

The cover element 50 at the left-hand end of the member 46 of the object holding means 14, in FIG. 2, has a through bore (not referenced) with a female screwthread 64 through which a screwthreaded spindle 66 is screwed. The screwthreaded spindle 66 has a shoulder or collar as indicated at 68 and extends with a stub portion 70 through a bearing arrangement 72 disposed on the guide member 32. Connected to the screwthreaded spindle 66 is a cutting thickness feed means 74 which is of per se known type and which has a controllable clutch device 76, of conventional kind, and a switching arm 78. A switch device as indicated at 80 in FIG. 1 is provided on the frame structure 10 of the microtome in such a way as to co-operate with the switching arm 78 of the cutting thickness feed means 74. The switch device 80 can be used to adjust the cutting thickness of a preparation which is to be thinly cut. For that purpose the switch means 80 can be in the form of a cam disc.

A lever element 84 is mounted on the guide member 32 pivotably about an axis indicated at 82 in FIG. 2. The lever element 84 embraces the screwthreaded spindle and extends in the vicinity of the shoulder or collar 68 thereon. The lever element 84 has an end portion which is remote from its axis 82 and on which a contact element 88 is carried. The contact element 88 is in the form for example of a roller. A switch element 90 is mounted on the guide member 32 pivotably by means of a peg 92 providing an axis for pivotal movement thereof. As can be clearly seen from FIG. 1, the switch element 90 is in the form of a doublearmed lever, having a first lever arm 94 which is longer than the second lever arm 96 which is in opposite relationship to the first lever arm 94, relative to the pivot mounting 92.

Reference numerals 98 and 100 in FIG. 1 identify first and second abutments which are disposed at stationary locations on the frame structure 10 of the microtome and which are arranged in the path of movement of the first lever arm 94 of the switch element 90. Reference numerals 102 and 104 in FIG. 1 identify third and fourth abutments which are disposed at stationary locations on the guide member 32.

The structure of the microtome according to the invention having been described, the mode of operation thereof will now be described as follows:

When, as a result of a rotary movement of the hand wheel 16 of the drive means 12 of the microtome the object holding means 14 is moved in the first direction in space as indicated by the arrow 36, from an upper position downwardly as indicated by the arrow 44 in FIG. 1, a thinly cut specimen is cut for example, by the cutting blade or knife 42, from an object (not shown) which is to be thinly cut, being clamped in the object holding means 14 or in the object clamping means 52 thereof. As soon as the object holding means 14 has reached the lowermost position in the first direction as indicated by the arrow 36, the first lever arm 94 of the switch element 90 comes into contact with the abutment 100 whereby the first lever arm 94 is pivoted through a given angle in a clockwise direction. When that happens, the curved switching surface 106 on the lever arm 94 comes to bear against the contact element 88 in such a way that the lever element is pivoted through a small angle in a clockwise direction about its axis as indicated at 82 in FIG. 2. When that happens the screwthreaded spindle 66 is set back by a defined distance, as indicated by an arrow 56 in FIG. 1. At the same time the spring element 108 which is disposed between the shoulder or collar 68 on the screwthreaded spindle 66 and the bearing arrangement 72 is mechanically stressed. Accordingly in the lower position of the object holding means 14, the object holding means 14 is moved back from the cutting plane 60 by a given distance, by virtue of operation of the switch element 90. When the hand wheel 16 is turned further, at the same time the object holding means 14 is moved in the direction indicated by the arrow 110 in FIG. 1 in the first direction 36, that is to say, the microtome produces a reversal movement of the object holding means 14 into the upper starting position in which the switch element 90 comes to bear with its first lever arm 94 against the upper abutment 98. In that condition the switch element 90 is switched over from the position shown in dash-dotted lines in FIG. 1 into the position shown in solid lines in FIG. 1, with the contact between the contact element 88 and the switching surface 106 of the switch element 90 being eliminated again. In that position in which the switch element 90 does not bear against the contact element 88, the spring element 108 is thus relieved again of the stressing applied thereto, thus reducing the stressing thereof to a minimum value which is predetermined by the surrounding structure, with the object holding means 14 performing an advance movement which is indicated by arrow 58 in FIG. 1. The advance movement 58 and the return movement 56 are in opposite directions to each other and are of the same amplitude. A corresponding point also applies in regard to the cutting movement as indicated by the arrow 44 and the reversal movement 110 which is in the opposite direction thereto.

In addition, in the upper position of the object holding means 14 the switching arm 78 of the cutting thickness feed means 74 comes to bear against the switching means 80 so that the switching arm 78 performs a pivotal movement about the longitudinal axis 54 through a given angle. That movement corresponds to a quite specific rotary movement of the screwthreaded spindle 66 through the last-mentioned angle and thus a cutting thickness feed movement of the object holding means 14 in the second direction indicated by the arrow 38. That cutting thickness feed movement is indicated by arrow 112 in FIG. 1. That is then again followed by a cutting movement as indicated by a broken-line arrow 44' in FIG. 1. That arrangement thus provides a pilgrim-type stepping movement in respect of the object holding means 14, with the number of steps of such movement corresponding to the number of revolutions of the hand wheel 16 of the drive means 12.

Although, as illustrated, the switch element 90 is in the form of a lever having first and second lever arms 94 and 96, it may also be of a different configuration, for example in the form of a single-armed lever. In that case the lever arm 94 may be provided with a recess into which projects an abutment on the guide member 32 in order to set a defined limit for the switching movement of the switch element 90.

It will be appreciated that the above-described construction of a microtome in accordance with the invention has been set forth solely by way of example and illustration of the invention and that various modifications and alterations may be made therein without thereby departing from the spirit and scope of the invention.

I claim:
1. A microtome, comprising:
   a frame structure;
   a cutting blade;
   an object holding means for holding an object to be cut by said cutting blade and movable with a linear oscillating movement in the frame structure, said object holding means including a guide member movable with a linear oscillating movement in a first direction in space by a drive means, and a holder member provided with an object clamping means and movable stepwise in a second direction in space which is normal to said first direction, and further including a spring element co-operable with said object holding means, wherein during an operating cycle said object clamping means performs a pilgrim stepping movement comprised of a cutting movement in said first direction whereby an object is cut by said blade, and a subsequent return movement in said second direction whereby the mechanical stressing of said spring element is increased, a reversal movement in said first direction and of the same amplitude as but in the opposite sense to said cutting movement, following said return movement, with the spring element in a stressed condition, a subsequent advance movement produced by a reduction in said increased stressing of said spring element and of the same amplitude as but in the opposite sense to said return movement, and a feed movement produced by a cutting thickness feed means, said cutting thickness feed means being located on the object holding means for advancing said object holding means during a drive cycle by a defined distance in an axial direction relative to the cutting plane defined by said blade;
   an object return means co-operable with said object holding means and adapted to return the object holding means by a given distance from said cutting plane after a cutting operation, said object return means including a switch element arranged on said object holding means and movable therewith in its oscillating movement, said switch element including a lever and being arranged on said guide member such that in a first position of said switch element, said mechanical stressing of said spring element is increased and in a second position of said switch element said mechanical stressing of said spring element is reduced; and
   first and second abutments disposed on said frame structure at the end portions of the path of movement of the switch element in its movement with said object holding means, said switch element being displaceable by said abutments between said first and second positions wherein in said first position of said switch element said object holding means is disposed in a position in which said object holding means is set back from said cutting plane and in said second position of said switch element said object holding means is in a position of being set forward toward the cutting plane.

2. A microtome as set forth in claim 1 wherein said holder member is a cylindrical member.

3. A microtome as set forth in claim 1 wherein said cutting thickness feed means comprises a screwthreaded spindle arranged in said second direction and said object holding means is mounted linearly displaceably but non-rotatably in said guide member and includes a portion having a female screwthread, wherein said spring element is operatively disposed between said guide member and said screwthreaded spindle, and further including a lever element having a first end portion mounted to the guide member pivotably about an axis oriented in said first direction, the lever element extending in a plane substantially normal to said second direction and co-operating with said screwthreaded spindle, the lever element having a second end portion co-operating with the object return means, the switch element being pivotable on said guide member about an axis oriented in a third direction in space normal to said first and second directions, and the switch element co-operating with its second end portion with said second end portion of the lever element thereby to increase the spring stressing of the spring element.

4. A microtome as set forth in claim 3 wherein said second end portion of the switch element which co-operates with said lever element has a curved switching surface.

5. A microtome as set forth in claim 3 wherein the switch element is in the form of a double-armed lever comprising a first lever arm cooperating with the lever element and an oppositely disposed second lever arm, the first lever arm being longer than the second lever arm.

6. A microtome as set forth in claim 5 wherein said guide member carries third and fourth abutments and said second lever arm of the switch element extends between said third and fourth abutments which thereby limit the switching movement of the switch element produced by the co-operation thereof with said first and second abutments.

* * * * *

UNITED STATES PATENT AND TRADEMARK OFFICE
CERTIFICATE OF CORRECTION

PATENT NO. : 4,967,629

DATED : November 6, 1990

INVENTOR(S) : Behme

It is certified that error appears in the above-identified patent and that said Letters Patent is hereby corrected as shown below:

Title Page

[30] "3809269" should read --3806269--.

Signed and Sealed this

Nineteenth Day of May, 1992

Attest:

DOUGLAS B. COMER

*Attesting Officer*  *Acting Commissioner of Patents and Trademarks*